(12) United States Patent
Heiss et al.

(10) Patent No.: US 8,610,434 B2
(45) Date of Patent: Dec. 17, 2013

(54) CRYOGEN-FREE COOLING SYSTEM FOR ELECTRON PARAMAGNETIC RESONANCE SYSTEM

(75) Inventors: Arthur H. Heiss, Brookfield, CT (US); Ajay Khatri, Bethleham, PA (US)

(73) Assignee: Coldedge Technologies, Inc., Allentown, PA (US)

( * ) Notice: Subject to any disclaimer, the term of this patent is extended or adjusted under 35 U.S.C. 154(b) by 327 days.

(21) Appl. No.: 13/188,270

(22) Filed: Jul. 21, 2011

(65) Prior Publication Data
US 2013/0021032 A1    Jan. 24, 2013

(51) Int. Cl.
*G01V 3/00* (2006.01)
(52) U.S. Cl.
USPC .................................. 324/316; 324/300
(58) Field of Classification Search
USPC ................... 324/300–322; 62/6, 610
See application file for complete search history.

(56) References Cited

U.S. PATENT DOCUMENTS

| | | | |
|---|---|---|---|
| 5,979,176 A * | 11/1999 | Stables et al. | 62/610 |
| 6,396,377 B1 | 5/2002 | Ying | |
| 6,725,670 B2 * | 4/2004 | Smith et al. | 62/6 |
| 7,143,586 B2 * | 12/2006 | Smith et al. | 62/6 |
| 7,586,305 B2 | 9/2009 | Hofer | |
| 8,464,542 B2 * | 6/2013 | Hilton et al. | 62/46.1 |
| 2010/0186425 A1 | 7/2010 | Veprik | |
| 2011/0005239 A1 | 1/2011 | Khatri | |
| 2011/0126553 A1 * | 6/2011 | Ball-DiFazio | 62/6 |

OTHER PUBLICATIONS

Perlson, B.D. and Weil J. A., Variable low temperature EPR cavity, The Review of Scientific Instruments, vol. 46, No. 7, pp. 874-878 Jul. 1975.
Weil J. A. and Schindler P., Variable Temperature EPR Cryostat Cavity, The Review of Scientific Instruments, vol. 38, No. 5, pp. 659-660 May 1961.

* cited by examiner

*Primary Examiner* — Brij Shrivastav
(74) *Attorney, Agent, or Firm* — O'Shea Getz P.C.

(57) ABSTRACT

In an electron paramagnetic resonance spectrometer, a closed cycle cryocooler is used to cool gaseous helium, which is then circulated around a sample to cool the sample by direct convection. Since the sample is not mechanically connected to the refrigerator, no vibrations are transmitted from the refrigerator to the sample and the sample can be quickly removed and replaced. The cooled helium can be passed through a Joule-Thomson expansion device before circulating the cooled helium around the sample to further cool the helium. In addition, a vacuum pump can be connected to the helium outlet after circulating the cooled helium around the sample to increase the pressure differential across the Joule-Thomson expansion device and further cool the helium. In order to raise the temperature of the cooled helium, a heater can be placed about the cooled helium line upstream from the sample.

21 Claims, 3 Drawing Sheets

CRYOGEN-FREE COOLING SYSTEM FOR ELECTRON PARAMAGNETIC RESONANCE SYSTEM

BACKGROUND

Electron paramagnetic resonance (EPR) or electron spin resonance (ESR) spectroscopy is a technique for studying chemical species that have one or more unpaired electrons, such as organic and inorganic free radicals or inorganic complexes that include a transition metal ion. According to quantum theory, an electron has a spin which can be understood as an angular momentum that produces a magnetic moment. If the electron is placed in a magnetic field the magnetic moment will tend to align with the magnetic field. However due to quantum effects, the electron can only have two states: one with the magnetic moment aligned parallel to the applied field and a second with the magnetic moment aligned anti-parallel to the field. Each of these two states has a different energy level. If electromagnetic radiation is applied at a frequency that corresponds to the separation between the two energy levels, energy is absorbed from the electromagnetic field and this absorption can be measured. An EPR spectrum can be produced by varying either the electromagnetic radiation frequency or the applied magnetic field strength and measuring the energy absorption. In practice, the latter is generally varied.

Because most stable molecules have all their electrons paired, the EPR phenomenon is not generally observable in those molecules. Some molecules, known as paramagnetic molecules, have an odd number of electrons, which obviously cannot be paired. It is these molecules that are commonly studied via EPR techniques. This limitation to paramagnetic species also means that the EPR technique is one of great specificity, since ordinary chemical solvents and matrices do not give rise to EPR spectra.

In many EPR experiments, it is either advantageous or necessary to measure the EPR sample at greatly reduced temperatures (4-10K). The advantages of operating at low temperature include an increase in signal levels from samples where relaxation times are very short at room temperature and the ability to study phase transitions.

There are several methods for cooling a sample to the range of several degrees Kelvin. The most widely used method is to immerse the sample in a bath of liquid helium. However, this method has several drawbacks. Liquid helium itself is relatively expensive and, if the liquid helium must be shipped to the work site, there is inevitably some loss of liquid helium due to boil-off, making the liquid helium even more expensive. Further, as the helium evaporates, the gas is generally vented to the atmosphere and lost so that typical experiments use several liters of liquid helium each. Since helium boil-off is continuous, it is not economical to allow the EPR apparatus to remain at low temperature between experiments, thus experiments must be conducted as rapidly as possible and scheduled together to conserve helium. Finally, changing the sample temperature away from the temperature of liquid helium is difficult and can only be accomplished by changing the pressure on the helium.

In order to overcome these difficulties, systems have been developed that do not use liquid helium. These systems generally use a closed-cycle refrigerator, such as a conventional Gifford-McMahon (GM) refrigerator or a pulse tube refrigerator to cool a metal "cold head" to the required temperature. The sample to be cooled is mounted on the cold head and cooled by direct conduction. These systems also have drawbacks. First, since the sample is mechanically connected to the cold head, any vibrations produced by the refrigeration mechanism are transferred to the sample. These vibrations are typically on the order of 1-2 hertz and can cause problems with the EPR experiments. Second, in order to insulate the cold head and the sample, these latter elements are typically enclosed in a housing which is evacuated. Therefore, the cold head must be brought to a raised temperature and the housing must be vented prior to changing the sample. After the sample has been changed, the housing must be evacuated and the cold head brought down to the correct temperature, both of which are time-consuming operations.

SUMMARY

In accordance with the principles of the invention, a closed cycle cryocooler is used to cool gaseous helium, which is then circulated around the sample to cool the sample by direct convection. Since the sample is not mechanically connected to the cryocooler, no vibrations are transmitted from the cryocooler to the sample and the sample can be quickly removed and replaced. Also since gaseous helium is used to cool the sample no liquid helium is required.

In one embodiment, the cryocooler cooled helium is passed through a Joule-Thomson expansion device before circulating the cooled helium around the sample to further cool the helium.

In another embodiment, a vacuum pump is connected to the helium outlet after circulating the cooled helium around the sample to increase the pressure differential across the Joule-Thomson expansion device and further cool the helium.

In still another embodiment, a heater is placed about the cooled helium line upstream from the sample in order to raise the temperature of the cooled helium.

DETAILED DESCRIPTION

Figure 1:
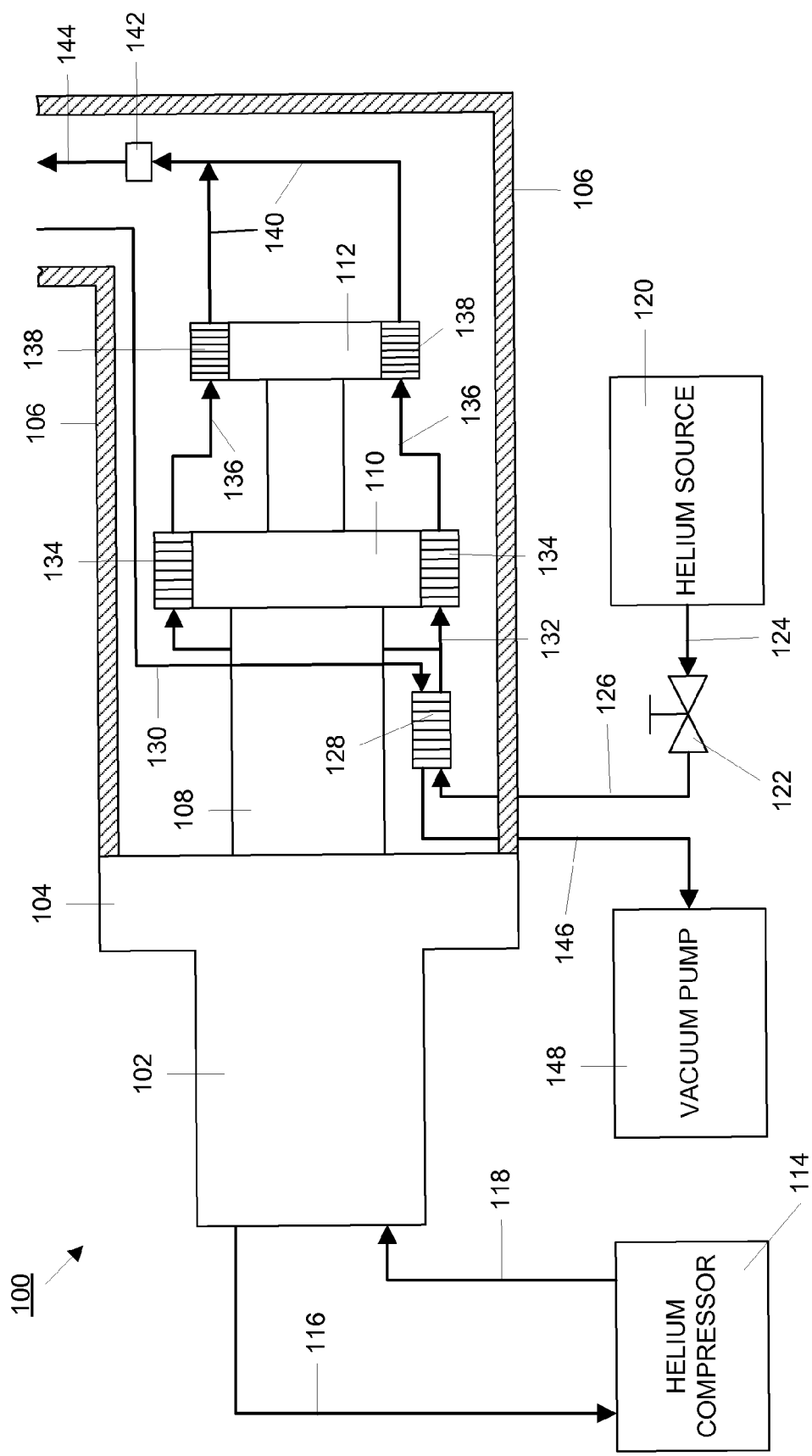
FIG. 1 shows a block schematic partial cross sectional diagram of the refrigeration system.

FIG. 1 shows a block schematic partial cutaway diagram of a cryocooler 100 constructed in accordance with the principles of the invention. The cryocooler uses a conventional closed-cycle cryocooler 102. This could be a conventional Gifford-McMahon cryocooler or a pulse tube cryocooler. Since the construction and operation of this type of cooler is well-known, the cooler will not be discussed in further detail herein. A cryocooler suitable for use with the invention is a model RDK 408D2 manufactured and sold by Sumitomo Cryogenics of America, Inc. 1833 Vultee Street Allentown, Pa. 18103-4783.

The cooler 102 is rotationally symmetrical and typically has a warm flange 104 onto which a vacuum housing 106 (shown cutaway) is attached. The interior of the vacuum housing is evacuated in order to insulate the cooler components. The vacuum housing 106 encloses the cooler body 108 in which a reciprocating piston (not shown) is located, a cooler first cold stage 110 and cooler second cold stage 112. In operation, the cooler 102 is supplied with gaseous helium from helium compressor 114 via line 118. Helium returns from the cooler 102 to the helium compressor 114 via return line 116.

In operation, the first cold stage 110 of the cooler 102 typically stabilizes at 30-35K (Kelvin) and the second cold stage 112 stabilizes at approximately 4K. Helium gas at room temperature (approximately 300K) from helium source 120 is supplied via line 124 to pressure valve 122 which controls the input helium pressure. Initially this pressure is set to 10-20 psi and later increased to 60-70 psi after the system cools down.

From pressure valve 122, the helium gas flows via line 126 into heat exchanger 128 where it exchanges heat with, and is cooled by, cooled helium gas returning from the sample chamber (described in detail below) via line 130.

The cooled helium gas exiting heat exchanger 128 passes via lines 132 to heat exchanger 134 which surrounds the cryocooler first cold stage 110. In heat exchanger 134 the gas is cooled to approximately 40K. From the heat exchanger 134, the cooler helium gas passes via lines 136 to a second heat exchanger 138 attached to the cryocooler second cold stage 112 where the gas is cooled to approximately between 4K and 10K.

Cooled helium gas exiting the heat exchanger 138 is supplied via output lines 140 to a conventional Joule-Thomson expansion device 142. When the gas passes through the expansion device 142, it expands into the sample chamber (shown in FIG. 2) via line 144. At this point the cooled helium gas is at approximately 4K.

Figure 2:
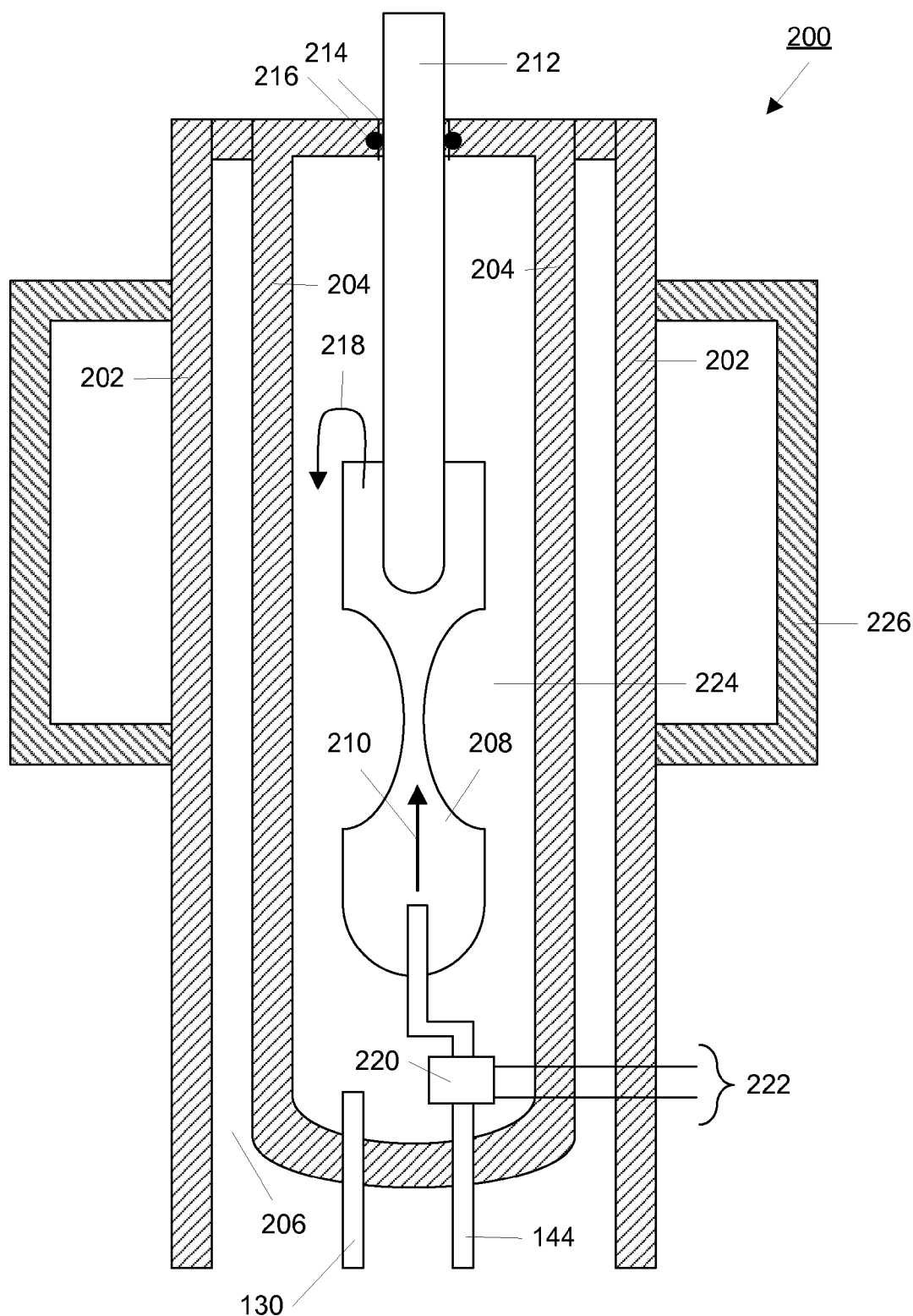
FIG. 2 shows a block schematic partial cross sectional diagram of the sample chamber.

FIG. 2 shows a cutaway view of the sample chamber 200. Chamber 200 is placed between the magnets of an EPR spectrometer (not shown). The sample chamber 200 has a double-wall jacket formed by walls 202 and 204. The space 206 between the walls 202 and 204 is connected to the interior of vacuum housing 106 so that the vacuum therein insulates the gas delivery apparatus 208 and the sample (not shown) in holder 212.

Holder 212 is a quartz sample tube commonly used in electron paramagnetic resonance (EPR) spectrometers and is inserted into the device through opening 214 which is sealed to the holder 212 via O-ring 216.

The cooled helium gas from the cryocooler apparatus 100 enters the sample chamber 200 via line 144 which discharges into the sample cooler 208 as indicated schematically by arrow 210. After flowing around the sample holder 212 and cooling the sample holder 212 and the sample by direct convection, the cooled gas exits the sample cooler 208 as indicated schematically by arrow 218 and returns to the cryocooler unit 100 via line 130.

The cooled helium gas may also be heated prior to entering the sample cooler 208 by means of a heater 220 which surrounds the gas entry line 144. This heater is typically an electrical resistance heater as indicated by leads 222, but may also be of another conventional design. The heater allows the temperature of the helium gas to be raised, thereby raising the sample temperature as necessary. Using this arrangement it is possible to control the temperature of the sample from approximately 4K to room temperature of 300K. A temperature sensor in heater 220 (not shown) can be used to control the heater 220 and maintain any desired temperature in the sample chamber 208.

It should be noted that the vacuum in space 206 is separated by wall 204 from the interior 224 of the sample chamber 200 where the pressure remains at the pressure of the expanded helium gas. Therefore, the sample can easily be changed by throttling back the helium gas supply via valve 122 and withdrawing the sample holder 212 through the O-ring 216. A new sample holder 212 can then be inserted and a new experiment begun by increasing the helium flow via valve 122. There is no requirement to vent the vacuum housing 106 or warm the cryocooler first and second cold stages 110, 112 in order to change samples.

In an EPR spectrometer, the sample holder 208 is conventionally located in a resonant cavity schematically illustrated as cavity 226. RF energy, typically in the microwave range is applied to cavity 226 via a waveguide (not shown in FIG. 2.)

It is also possible to reduce the temperature of the cooling helium gas by placing a vacuum pump 148 on the output 146 of heat exchanger 128. The vacuum pump 148 reduces the pressure in the sample chamber 200 and thereby increases the pressure differential across the Joule-Thomson expansion device 142. By reducing the pressure of the helium on the sample side, the temperature of the cooling helium gas in the sample cooler 208 can be reduced to 3K or less.

Although cooling gaseous helium is typically vented to the atmosphere via line 146 or vacuum pump 148, the inventive system uses much less helium than a conventional liquid-helium cooled system. This is because one liter of liquid helium expands to 768 liters of gaseous helium. Further, gaseous helium can easily be shipped in tanks without loss. The inventive system can also efficiently be idled between experiments without allowing the cooling system to warm to room temperature by throttling back the helium pressure at the inlet 126 via valve 122 to 2-10 psi. This helium flow maintains the temperature of the cooling helium in the sample cooler 208 at approximately 10-12K between experiments without excessive helium loss.

Figure 3:
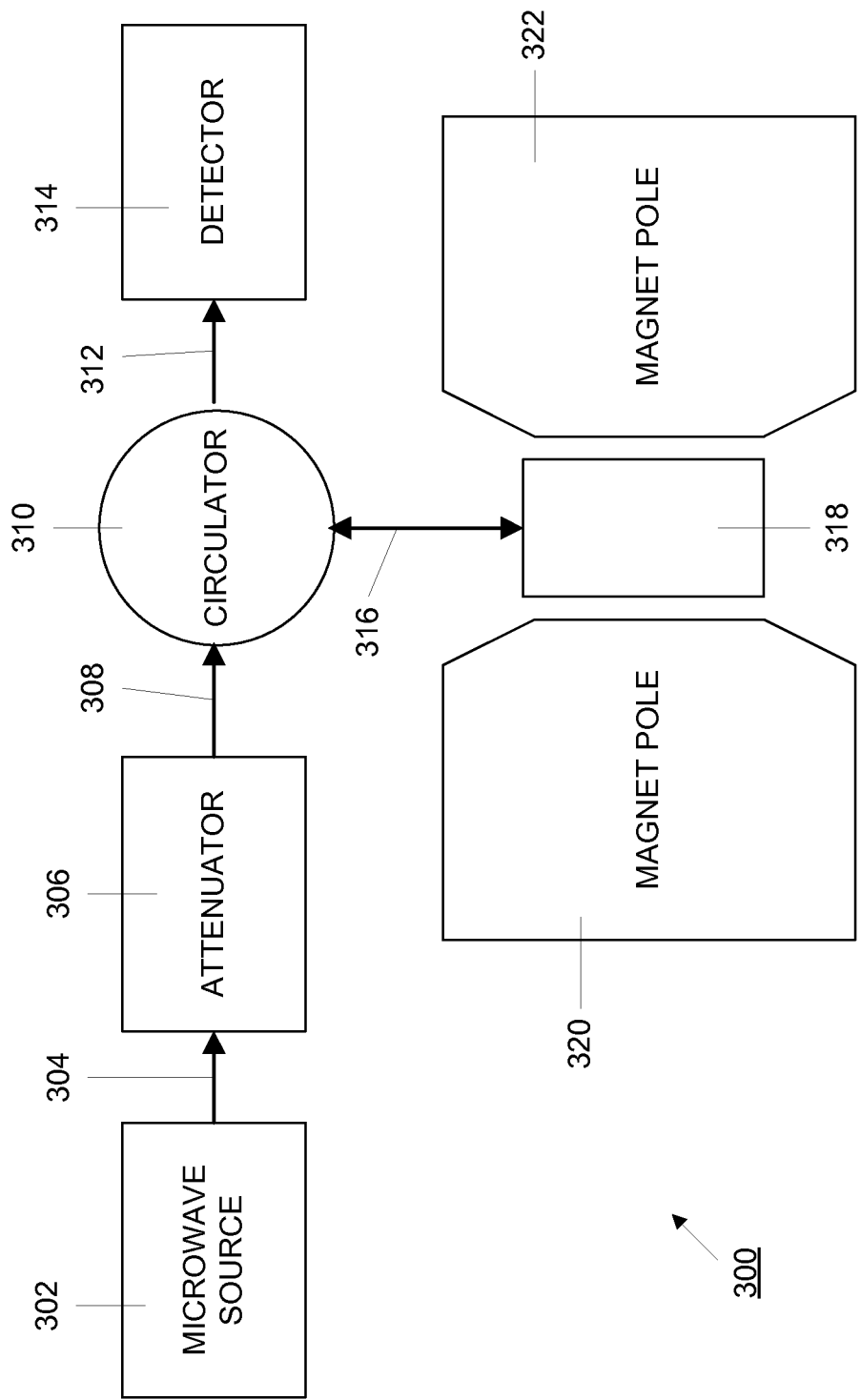
FIG. 3 is a block schematic diagram showing the main components of an EPR spectrometer.

FIG. 3 illustrates in a very schematic form, the major components of an EPR spectrometer 300. Microwave source 302 generates microwave RF radiation and applies the radiation to an attenuator 306 as schematically illustrated by arrow 304. Attenuator 306 attenuates the radiation to a level suitable for performing measurements and provides the attenuated radiation to a circulator 310. Circulator 310 is a non-linear device that directs the radiation, via waveguide 316 to the resonant cavity 318 that surrounds the sample (not shown.) The resonant cavity 318 is located between the poles 320, 322 of a magnet.

Energy exiting the cavity 318 is directed, via waveguide 316, back to circulator 310. Circulator 310, in turn, directs the energy to detector 314 as schematically illustrated by arrow 312 which detects energy absorbed by the sample.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A cryogen-free cooling system for cooling a sample, comprising:
   a closed cycle cryocooler having a cold stage;
   a first heat exchanger mounted on the cold stage;
   a Joule-Thomson expansion device;
   a sample chamber surrounding the sample; and
   piping for conducting gaseous helium from a helium source through the heat exchanger, from the heat exchanger to the expansion device and from the expansion device to the sample chamber, so that cooled gaseous helium circulates around the sample in the sample chamber and cools the sample directly by convection.

2. The cooling system of claim 1 wherein the cryocooler has a first cold stage and a second cold stage, the first heat exchanger is mounted on the first cold stage and a second heat exchanger is mounted on the second cold stage.

3. The cooling system of claim 2 wherein the piping conducts gaseous helium from a helium source through the first heat exchanger to the second heat exchanger and from the second heat exchanger to the Joule-Thomson expansion device.

4. The cooling system of claim 1 further comprising a vacuum housing which surrounds the cryocooler, the heat exchanger and the expansion device and extends as a jacket around the sample chamber.

5. The cooling system of claim 1 further comprising a second heat exchanger through which gaseous helium from the helium source passes before entering the first heat exchanger, the helium exchanging heat in the second heat exchanger with helium exiting the sample chamber.

6. The cooling system of claim 1 further comprising a vacuum pump connected to the second heat exchanger for increasing a pressure differential across the expansion device.

7. The cooling system of claim 1 wherein the sample chamber comprises an enclosed volume having a open-ended sample cooler therein that surrounds the sample and into which cooled gaseous helium from the expansion device flows.

8. The cooling system of claim 7 wherein the enclosed volume has an opening therein through which the sample can be inserted into the sample chamber.

9. The cooling system of claim 8 wherein the sample is contained in a sample holder which is inserted into the sample chamber through the opening and sealed by an O-ring surrounding the opening.

10. The cooling system of claim 1 further comprising a heater for heating cooled gaseous helium exiting the expansion device into order to increase sample temperature.

11. A method for cooling a sample, comprising:
(a) providing a cryogen-free cooling system having a closed cycle cryocooler with a cold stage, a first heat exchanger mounted on the cold stage, a Joule-Thomson expansion device and a sample chamber surrounding the sample; and
(b) conducting gaseous helium from a helium source through the heat exchanger, from the heat exchanger to the expansion device and from the expansion device to the sample chamber, so that cooled gaseous helium circulates around the sample in the sample chamber and cools the sample directly by convection.

12. The method of claim 11 wherein the cryocooler has a first cold stage and a second cold stage, the first heat exchanger is mounted on the first cold stage and a second heat exchanger is mounted on the second cold stage.

13. The method of claim 12 wherein step (b) comprises conducting gaseous helium from a helium source through the first heat exchanger to the second heat exchanger and from the second heat exchanger to the Joule-Thomson expansion device.

14. The method of claim 11 wherein step (a) comprises providing a vacuum housing which surrounds the cryocooler, the heat exchanger and the expansion device and extends as a jacket around the sample chamber.

15. The method of claim 11 wherein step (a) comprising providing a second heat exchanger through which gaseous helium from the helium source passes before entering the first heat exchanger, the helium exchanging heat in the second heat exchanger with helium exiting the sample chamber.

16. The method of claim 11 further comprising connecting a vacuum pump to the second heat exchanger for increasing a pressure differential across the expansion device.

17. The method of claim 11 wherein step (a) comprises providing in the sample chamber an enclosed volume having a open-ended sample cooler therein that surrounds the sample and into which cooled gaseous helium from the expansion device flows.

18. The method of claim 17 wherein the enclosed volume has an opening therein through which the sample can be inserted into the sample chamber.

19. The method of claim 18 wherein the sample is contained in a sample holder and the method further comprises inserting the sample holder into the sample chamber through the opening and using an O-ring surrounding the opening to provide a seal around the sample holder.

20. The method of claim 11 further comprises heating cooled gaseous helium exiting the expansion device into order to increase sample temperature.

21. An electron paramagnetic resonance spectrometer for performing measurements on a sample, comprising:
a magnet having two poles;
a closed cycle cryocooler having a cold stage;
a first heat exchanger mounted on the cold stage;
a Joule-Thomson expansion device;
a sample chamber surrounding the sample and positioned between the two magnet poles;
piping for conducting gaseous helium from a helium source through the heat exchanger, from the heat exchanger to the expansion device and from the expansion device to the sample chamber, so that cooled gaseous helium circulates around the sample in the sample chamber and cools the sample directly by convection;
means for applying RF radiation to the sample; and
a detector for detecting RF radiation absorbed by the sample.

* * * * *